United States Patent
Ma et al.

(10) Patent No.: US 6,737,526 B1
(45) Date of Patent: May 18, 2004

(54) METHOD FOR PREPARING MELAMINE SALT OF BIS-(PENTAERYTHRITOL PHOSPHATE) PHOSPHORIC ACID

(75) Inventors: Chong Ma, Tao-Yuan (TW); Tseng-Rong Wu, Tao-Yuan (TW); Yuen-Hsin Peng, Tao-Yuan (TW)

(73) Assignee: Chung-Shan Institute of Science & Technology, Tao Yuan (TW)

( * ) Notice: Subject to any disclaimer, the term of this patent is extended or adjusted under 35 U.S.C. 154(b) by 0 days.

(21) Appl. No.: 10/303,784

(22) Filed: Nov. 26, 2002

(51) Int. Cl.[7] ............... C07D 251/22; C07F 9/6571
(52) U.S. Cl. ........................ 544/195; 558/74
(58) Field of Search .................. 544/195; 558/74

(56) References Cited

U.S. PATENT DOCUMENTS 4,478,998 A * 10/1984 Halpern et al. ............. 544/195

* cited by examiner

Primary Examiner—Robert W. Ramsner
Assistant Examiner—Ebenezer Sackey
(74) Attorney, Agent, or Firm—Bacon & Thomas, PLLC

(57) ABSTRACT

Bis-(pentaerythritol phosphate) phosphoric acid is prepared by mechanochemical synthesis including ball milling a mixture containing $P_2O_5$, pentaerythritol, an alkyl benzene having one or two C1–C5 alkyl groups, and a metal halide catalyst, in a ball mill as a reactor and at a temperature of room temperature to 150° C. Melamine is then reacted with the resulting bis-(pentaerythritol phosphate) phosphoric acid to form a product of melamine salt thereof.

11 Claims, No Drawings

METHOD FOR PREPARING MELAMINE SALT OF BIS-(PENTAERYTHRITOL PHOSPHATE) PHOSPHORIC ACID

BACKGROUND OF THE INVENTION

U.S. Pat. No. 4,454,064 discloses a method for preparing pentaerythritol phosphate, which comprises reacting pentaerythritol with $POCl_3$ in dioxane solvent at 75–125° C. The pentaerythritol phosphate thus prepared can be used as an intermediate for synthesizing a polyurethane flame retardant and a plasticizer. This preparation method will also generate HCl gas and a residual solution of excessive $POCl_3$.

U.S. Pat. No. 4,478,998 discloses a synthesis of an amino-s-triazine salt of a phosphoric acid having the following formula:

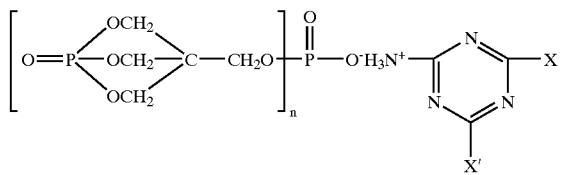

when X and X' in the formula are amino, said salt is melamine salt of bis-(pentaerythritol phosphate) phosphoric acid. The synthesized amino salt can be used as a flame retardant additive for certain polymer compositions. In Example 1 of said patent, melamine reacts with acid chloride of bis-(pentaerythritol phosphate) phosphoric acid in water to obtain said melamine salt. Said acid chloride of bis-(pentaerythritol phosphate) phosphoric acid is synthesized through the following reaction formula:

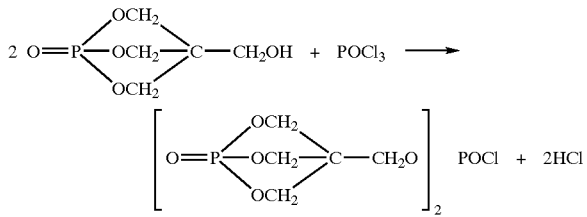

HCl gas and a residual solution of excessive $POCl_3$ will also be generated in the abovementioned reaction.

SUMMARY OF THE INVENTION

The present Invention provides a method for preparing a melamine salt of bis-(pentaerythritol phosphate) phosphoric acid, which comprises preparing bis-(pentaerythritol phosphate) phosphoric acid, and reacting melamine with the obtained bis-(pentaerythritol phosphate) phosphoric acid to form a melamine salt thereof. The preparation of bis-(pentaerythritol phosphate) phosphoric acid according to the present invention has the following characteristics:

1. The method uses $P_2O_5$ as a reactant.
2. The method uses a mechanochemical synthesis and uses a ball mill as a reactor.
3. The method uses an alkyl benzene, such as toluene or xylene, as a solvent. The alkyl benzene may have one or two identical or different alkyls having 1 to 5 carbons.
4. The solvent used in the method is at room temperature or pre-heated to 50–150° C.
5. The method uses metal halide $MX_2$, such as $MgCl_2$ etc., as a catalyst, wherein M=Mg, Zn, or Al; and X=Cl, or Br. The weight ratio of the catalyst to pentaerythritol is 1:99 to 5:95.

Compared to the conventional process, the present invention has the following three advantages: (a) no generation of waste gas of HCl; (b) free of a waste aqueous solution generated from neutralization of HCl waste gas; and (c) avoiding handling of a residue solution containing unreacted $POCl_3$.

The reaction between melamine and bis-(pentaerythritol phosphate) phosphoric acid according to the present invention can be carried out in a ball mill or a conventional mechanical agitation reactor, which comprises ball-milling or mechanically mixing a mixture of melamine, bis-(pentaerythritol phosphate) phosphoric acid, and a solvent at room temperature to 100° C. Suitable solvents include (but not limited to) water, acetonitrile ($CH_3CN$), and a mixture of the solvent used in the preparation of bis-(pentaerythritol phosphate) phosphoric acid with acetonitrile. Preferably, said solvent is pre-heated to 50–100° C. and thus there is no heating while ball milling said mixture. More preferably, said solvent is a mixture of toluene with acenonitrile preheated to 50–80° C., acetonitrile that has been pre-heated to 80° C. or boiling water, most preferably is boiling water.

DETAILED DESCRIPTION OF THE PRESENT INVENTION

The present invention discloses a method for preparing melamine salt of bis-(pentaerythritol phosphate) phosphoric acid, which comprises preparing bis-(pentaerythritol phosphate) phosphoric acid, and reacting melamine with the obtained bis-(pentaerythritol phosphate) phosphoric acid to form a melamine salt thereof. Several factors affecting the synthesis of said bis-(pentaerythritol phosphate) phosphoric acid are discussed in the following:

1. Study on the Reaction Solvent

The molecular structure unit of phosphorus pentoxide is $P_4O_{10}$, usually represented by $P_2O_5$. Phosphorus pentoxide is a very strong dehydration agent, and is liable to react with water to form phosphoric acid.

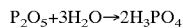

Furthermore, it can grab $H_2O$ from reactant molecules to form metaphosphoric acid and related inorganic or organic material, e.g.

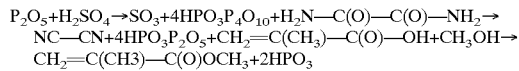

$P_2O_5$ reacts with ethyl ether to form triethyl phosphate:

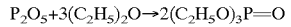

The strong reactivity of phosphorus pentoxide makes the selection of the reaction solvent greatly restricted. The inventors of the present invention have tried using a solvent such as n-hexane, diethyl phosphate, and toluene, etc. for performing the reaction, in which the reaction of using n-hexane as a solvent is not ideal and has an extremely low yield. When diethyl phosphate is used as a solvent, the reaction has a very good yield. However, since the properties of diethyl phosphate are too close to the properties of the product bis-(pentaerythritol phosphate) phosphoric acid, they are difficult to be separated. Therefore, toluene is selected as a reaction solvent.

Pentaerythritol can be dissolved in diethyl phosphate solvent, therefore, after addition of $P_2O_5$, the reaction can take place at a reaction temperature of 90° C. While not dissolving in toluene, pentaerythritol will turn into a molten state when the temperature rises to 90° C. and can react with $P_2O_5$. Since pentaerythritol in its molten state has an extremely high viscosity and is difficult to agitate, the reaction yield is not high. Therefore, how to achieve an ideal agitation for pentaerythritol to have a sufficient contact with $P_2O_5$ is a key factor in increasing the yield. Pentaerythritol does not dissolve at the boiling point of n-hexane at 68° C. and has no change in state at this temperature, this could be a reason why it does not react with $P_2O_5$ in n-hexane.

2. Study on Reaction Temperature

Pentaerythritol does not react with $P_2O_5$ in toluene solvent at a temperature lower than 70° C. under traditional stirring process. When the temperature increases to 90° C., pentaerythritol can undergo a phosphate esterification reaction. The reaction time is about 10 hours. When the temperature rises to 105° C., the reaction time can be reduced to 6 hours.

3. Effects of the Particle Size of Pentaerythritol

The reaction yield and purity can be increased when, prior to the reaction, pentaerythritol is ground in toluene in a ball mill.

4. Ball Mill Process

Based on the above studies 1~3, the key factors affecting the method of the present invention include: heating of the solvent, material with a fine particle size, and complete mixing in the reaction. Therefore, a ball mill is considered as a reactor to achieve a complete grinding, mixing and thermal insulation in the reaction. A suitable reaction time is 4–20 hours.

5. Formation of Phosphoric Acid in the Reaction

When 2 moles of pentaerythritol reacts with 1.5 mole of $P_2O_5$, 1 mole of bis-(pentaerythritol phosphate) phosphoric acid and 3.5 moles of water will be generated. Since 3 moles of water will react with 1 mole of $P_2O_5$ to from 2 moles of phosphoric acid, and a consumption of $P_2O_5$ occurs. Therefore, an excessive amount of $P_2O_5$ should be used for all the pentaerythritol phosphate alcohol to be converted to bis-(pentaerythritol phosphate) phosphoric acid. A suitable mole ratio of pentaerythritol to $P_2O_5$ is 4:3 to 1:2.

The reaction between melamine and bis-(pentaerythritol phosphate) phosphoric acid according to the present invention can be carried out in said ball mill or a conventional mechanical agitation reactor, preferably in a ball mill. The reaction can be carried out using acetonitrile or water as the solvent. According to the present invention, when the conventional mechanical mixing is used and acetonitrile is used as a solvent, the reaction can be completed in 6 hours by reflux. In the ball mill process where acetonitrile which is pre-heated to 80° C. is used, the reaction time is 7.5 hours. In the ball mill process, if toluene is still used as a solvent in the reaction for forming melamine salt after the preparation of bis-(pentaerythritol phosphate) phosphoric acid, the result is poor. After the completion of the preparation of bis-(pentaerythritol phosphate) phosphoric acid in the ball mill process, if the original solvent (400 ml) is retained and another 100 ml of acetonitrile, which is pre-heated to 80° C., is added as a solvent in the reaction for forming melamine salt, the reaction can be carried out smoothly and the reaction time is also 7.5 hours. Furthermore, if the remaining solvent is poured out and boiling water is added as a solvent in the reaction for forming melamine salt, the reaction time can be greatly reduced to 15–60 minutes. The obtained melamine salt of bis-(pentaerythritol phosphate) phosphoric acid has a good heat resistance, only about 10~20% of which will be decomposed at 200~300° C., and about 40% of which will remain at a temperature exceeding 600° C.

The present invention uses $P_2O_5$ to replace $POCl_3$, and a mechanochemical synthesis process to overcome lack of a suitable solvent. Thus, the present invention has the following advantages: no formation of hydrochloric acid, no waste solution, environmentally friendly, without the need of heating in the reaction, high yield, Increased purity, and capability of recycling solvent.

The reaction formulas involved in the following Examples are shown in the following:

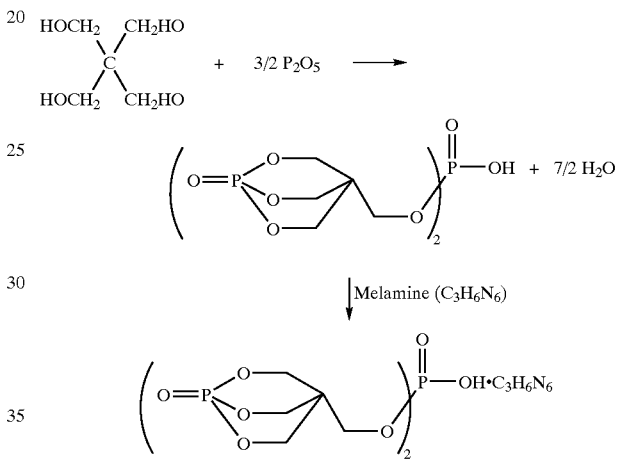

Since $P_2O_5$ will be consumed by the 7/2 moles of water simultaneously formed during the reaction, an excessive amount of $P_2O_5$ is needed in the reaction. Therefore, a small amount of $H_3PO_4$ will be also formed together with the product as shown in the following reaction:

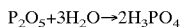

Since $P_2O_5$ is very hygroscopic, the feeding must be carried out by using an enclosed feeding device for solid feed.

EXAMPLE 1

Ball Mill Process for Synthesis of bis-(pentaerythritol phosphate) Phosphoric Acid (Abbreviated as b-PEPAP)

A ball mill reactor with one liter capacity was used and ceramic balls with a diameter of 2 cm were used.

13.6 g (0.1 mol) of pentaerythritol and 18.88 g (0.133 mol) of $P_2O_5$ were used. 400 ml of toluene was used and was pre-heated to 90~100° C. After drying, the ball mill reactor was added with the pre-heated solvent, and sequentially added with pentaerythritol, $P_2O_5$, and 0.4 g of $MgCl_2$, followed by ceramic balls. The ball mill reactor was then closed and rotated. The reaction was carried out for 6 hours. After the reaction, the liquid portion in the ball mill reactor was poured out, and the remaining product mixture was subjected to a reduced pressure to evaporate the solvent contained therein. $^{31}$P-NMR spectrum of the product mixture was taken and the integration areas of bis-(pentaerythritol phosphate) phosphoric acid (b-PEPAP) and phosphoric acid therein were calculated, thereby obtaining the phosphor content ratios thereof, wherein the relative phosphor content ratio of b-PEPAP to phosphoric value is 56 to 44. The phosphor content ratio was used to calculate the purity of b-PEPAP in the product mixture, which is 65 wt %.

$^{31}$P-NMR was used to Identify the main components in the product mixture obtained by the mechanochemical synthesis ball mill process in Example 1, wherein DMSO $d_6$ was used as a solvent. The results Indicate that the resonance at 0.4 ppm was phosphoric acid, −0.3 ppm was P—OH, −6.4 ppm was P on the bicyclo ring (pentaerythritol phosphate alcohol, as shown in Example 1 of EP 0 578 318 A1).

Preparation of Melamine Salt of bis-(pentaerythritol Phosphate) Phosphoric Acid (Abbreviated as b-PEPAP.MEL)

EXAMPLE 2

The product mixture of Example 1 was retained in the ball mill reactor, after the liquid portion was poured out. 21 g (0.166 mol) of melamine was poured into the ball mill, and 300 ml of acetonitrile which was pre-heated to 80° C. was added. The ball mill reactor was closed and rotated for 6 hours. $^{31}$P-NMR spectrum of a sample of the reaction solution taken from the ball mill reactor showed no existence of $^{31}$P peak, which Indicated that b-PEPAP and phosphoric acid were all consumed. The product b-PEPAP.MEL and the by-product melamine salt of phosphoric acid were all insoluble in acetonitrile solvent. The reaction was completed with a conversion rate of 100%.

EXAMPLE 3

The procedures in Example 2 were repeated except that the liquid portion of the reaction mixture in the ball mill reactor was not poured out, 100 ml of acetonitrile which was pre-heated to 80° C. was added instead of 300 ml, and the ball mill reactor was for 7.5 hours. The conversion rate was 100%.

EXAMPLE 4

The procedures in Example 2 were repeated except that 350 ml of pre-heated boiling water was added Instead of acetonitrile, and the ball mill reactor was rotated for 15 minutes only. $^{31}$P-NMR spectrum of a sample of the reaction solution taken from the ball mill reactor showed no existence of 31P peak. The reaction was completed with a conversion rate of 100%.

The melamine salt of bis-(pentaerythritol phosphate) phosphoric acid obtained in Example 2 to Example 4 had an average particle size of 6–8 μm, and the particle size distributions thereof showed that 91% of the particles were smaller than 14.4 μm. Their IR spectrums were substantially the same and contained the following major characteristic absorption wavelength:

900~1060 (broad): P—O—CH$_2$R (Vibration)
1164~1185 (strong): P=O (Vibration)
1430~1548 (medium): primary amine salt, bending
1650 (wide, strong): O=P—OH
3100 (strong): amine salt, primary
3300 (medium): primary amine

What is claimed is:

1. A method for preparing a melamine salt of bis-(pentaerythritol phosphate) phosphoric acid by a mechanochemical synthesis, which comprises the following steps: (a) ball milling a mixture comprising P$_2$O$_5$, pentaerythritol, an alkyl benzene having one or two C1–C5 alkyl groups, and a metal halide catalyst in a ball mill reactor at a temperature of room temperature to 150° C. to form bis-(pentaerythritol phosphate) phosphoric acid; and (b) ball milling or mechanically mixing a mixture comprising melamine, bis-(pentaerythritol phosphate) phosphoric acid and a solvent at room temperature to 100° C., wherein said solvent is water, acetonitrile, or a mixture of the solvent in step (a) with acetonitrile.

2. The method as claimed in claim 1, wherein said alkyl benzene is toluene, and said metal halide catalyst has a chemical formula of MX$_2$, wherein M is Mg, Zn or Al, and X is Cl or Br.

3. The method as claimed in claim 2, wherein said metal halide catalyst is MgCl$_2$.

4. The method as claimed in claim 1, wherein a molar ratio of pentaerythritol to P$_2$O$_5$ in said mixture of Step (a) is 4:3 to 1:2.

5. The method as claimed in claim 1, wherein a weight ratio of said catalyst to pentaerythritol in said mixture of Step (a) is 1:99 to 5:95.

6. The method as claimed in claim 1, wherein said ball milling in Step (a) is carried out for 4–20 hours.

7. The method as claimed in claim 1, wherein said temperature in Step (a) is 90–105° C.

8. The method as claimed in claim 2, wherein said toluene in Step (a) is pre-heated to a temperature of 90–100° C. prior to being added to said ball mill reactor; and said ball milling in Step (a) is carried out without heating.

9. The method as claimed in claim 1, wherein said solvent in Step (b) is pre-heated to 50–100° C., and said mixture in step (b) is ball milled in said ball mill reactor without heating.

10. The method as claimed in claim 9, wherein said solvent is a mixture of toluene with acetonitrile pre-heated to 50–80° C., acetonitrile pre-heated to 80° C., or boiling water.

11. The method as claimed in claim 10, wherein said solvent is boiling water.

* * * * *